United States Patent
Morgan et al.

(10) Patent No.: US 8,865,137 B2
(45) Date of Patent: Oct. 21, 2014

(54) DENTIFRICE COMPOSITION

(75) Inventors: Andre Morgan, Robbinsville, NJ (US);
Venda Porter, Piscataway, NJ (US);
Melissa Martinetti, Bridgewater, NJ (US); Michael Prencipe, West Windsor, NJ (US)

(73) Assignee: Colgate-Palmolive Company, New York, NY (US)

( * ) Notice: Subject to any disclaimer, the term of this patent is extended or adjusted under 35 U.S.C. 154(b) by 213 days.

(21) Appl. No.: 13/266,998

(22) PCT Filed: May 25, 2010

(86) PCT No.: PCT/US2010/036041
§ 371 (c)(1),
(2), (4) Date: Oct. 28, 2011

(87) PCT Pub. No.: WO2010/138492
PCT Pub. Date: Dec. 2, 2010

(65) Prior Publication Data
US 2012/0045402 A1 Feb. 23, 2012

Related U.S. Application Data

(60) Provisional application No. 61/181,116, filed on May 26, 2009, provisional application No. 61/181,124, filed on May 26, 2009.

(51) Int. Cl.
*A61Q 11/00* (2006.01)
*A61K 8/73* (2006.01)
*A61K 8/365* (2006.01)
*A61K 8/27* (2006.01)

(52) U.S. Cl.
CPC .............. *A61Q 11/00* (2013.01); *A61K 8/731* (2013.01); *A61K 8/365* (2013.01); *A61K 8/27* (2013.01)
USPC ........................................................ 424/57

(58) Field of Classification Search
USPC ........................................................ 424/57
See application file for complete search history.

(56) References Cited

U.S. PATENT DOCUMENTS

| | | |
|---|---|---|
| 4,022,880 A | 5/1977 | Vinson et al. |
| 4,138,477 A | 2/1979 | Gaffar |
| 4,820,506 A | 4/1989 | Kleinberg et al. |
| 4,839,157 A | 6/1989 | Mei-King Ng et al. |
| 4,900,552 A | 2/1990 | Sanvordeker et al. |
| 5,047,244 A | 9/1991 | Sanvordeker et al. |
| 5,695,746 A | 12/1997 | Garlick, Jr. et al. |
| 5,700,478 A | 12/1997 | Biegajski et al. |
| 5,948,430 A | 9/1999 | Zerbe et al. |
| 6,123,965 A | 9/2000 | Jacob et al. |
| 6,241,974 B1 | 6/2001 | White, Jr. et al. |
| 6,287,541 B1 | 9/2001 | Creeth et al. |
| 6,315,986 B1 | 11/2001 | Wong et al. |
| 6,596,298 B2 | 7/2003 | Leung et al. |
| 6,669,929 B1 | 12/2003 | Boyd et al. |
| 2003/0053962 A1 | 3/2003 | Zerbe et al. |
| 2003/0054034 A1 | 3/2003 | Leung et al. |
| 2004/0126332 A1 | 7/2004 | Boyd et al. |
| 2005/0019273 A1 | 1/2005 | Boyd et al. |
| 2006/0134020 A1* | 6/2006 | Robinson et al. ............... 424/52 |
| 2007/0020201 A1* | 1/2007 | Boyd et al. ...................... 424/52 |
| 2008/0112903 A1* | 5/2008 | Montgomery ................... 424/57 |
| 2008/0138369 A1 | 6/2008 | Boyd et al. |

FOREIGN PATENT DOCUMENTS

| | | |
|---|---|---|
| WO | WO 01/34108 | 5/2001 |
| WO | WO 03/015749 | 2/2003 |
| WO | WO 2004/060335 | 7/2004 |
| WO | WO 2007/013937 | 2/2007 |
| WO | WO 2007/076466 | 7/2007 |
| WO | WO 2008/041055 | 4/2008 |
| WO | WO 2008/130764 | 10/2008 |
| WO | WO 2010/114546 | 10/2010 |

OTHER PUBLICATIONS

Reynolds EC. Contents of Toothpaste—Saftey Implications. Australian Prescriber. 1994; 17: 49-51.*
Gan et al., 2009, "Antibacterial Activity of Zinc-Chelator Complexes," The Preliminary Program for IADR/AADR/CADR 87th General Session and Exhibition (Apr. 1-4, 2009).
Hider et al., 1990, "Facilitated uptake of zinc into human erythrocytes. Relevance to the treatment of sickle-cell anaemia," Biochem. Pharmacol. 39(6):1005-1012.
International Search Report and Written Opinion in International Application No. PCT/US10/036041, mailed Mar. 28, 2011.
International Search Report and Written Opinion in International Application No. PCT/US10/036140, mailed Mar. 25, 2011.
International Search Report and Written Opinion in International Application No. PCT/US10/036143, mailed Mar. 25, 2011.

(Continued)

*Primary Examiner* — Paul Zarek
(74) *Attorney, Agent, or Firm* — Howard C. Lee

(57) ABSTRACT

Disclosed are dentifrice compositions comprising an orally acceptable vehicle and at least one source of metal ions in a polymer matrix, the metal being selected from zinc, stannous, copper or combinations thereof, the at least one source of metal ions comprising from 10 to 75 wt % of the total weight of the polymer matrix and the at least one source of metal ions, and wherein the dentifrice composition comprises less than 10 wt % water based on the total weight of the dentifrice composition. Also disclosed is a method of stabilizing at least one source of metal ions in a dentifrice compositions.

20 Claims, No Drawings

(56) References Cited

OTHER PUBLICATIONS

Majithiya et al., 2008, "Mucoahesion Enhancement: Enhancement of Mucoadhesion by Blending Anionic, Cationic & Nonionic Polymers," Drug Delivery Tech. 8:40-45.

Muller et al., 1996, "The Effect of pH on the Corrosion Inhibition of Zinc Pigments by Phenol Derivatives," Corrosion Science 38(11):1869-1875.

Vasir et al., 2003, "Bioadhesive microspheres as a controlled drug delivery system," Int. J. Pharmaceutics 255(1-2):13-32.

* cited by examiner

DENTIFRICE COMPOSITION

CROSS REFERENCE TO RELATED APPLICATIONS

This application is a national stage entry under 35 U.S.C. §371 of International Patent Application No. PCT/US2010/036041, filed 25 May 2010, which claims priority to U.S. Provisional Patent Application No. 61/181,116, filed on 26 May 2009, and U.S. Provisional Patent Application No. 61/181,124, filed on 26 May 2009, all of which are incorporated herein by reference.

FIELD

The present invention relates to a dentifrice composition and to a method of stabilizing metal ions in a dentifrice composition.

BACKGROUND

It is known to provide dentifrice compositions including a source of metal ions for delivery to the oral cavity during brushing of the teeth. Such metal ions can act as therapeutic agents. Some metal ions tend to be unstable in dentifrice compositions, particularly when the dentifrice composition includes components with which the metal ions may react during manufacture or storage of the dentifrice composition prior to use. This reduces the delivery and bioavailability of the metal ions at the oral surfaces during brushing of the teeth when using the dentifrice.

U.S. Pat. No. 6,669,929 (Boyd et al.) and the related U.S. Patent Application Publication Nos. 2004/0126332 and 2008/0138369 disclose a dentifrice containing functional film flakes. The film flakes are formed of a water hydratable film which forms a matrix having entrained therein a constituent which may be a therapeutic material, or a cosmetic or decorative material. A number of therapeutic materials are disclosed, including fluoride salts as anticavities agents, calcium salts, anticalculus agents and other active agents including antibacterial agents, breath freshening agents, desensitizers, vitamins, herbs, whitening agents, high cleaning silica, preservatives, silicones or chlorophyll compounds. The breath freshening agents identified are zinc gluconate, zinc citrate and/or alpha ionone.

There is a need in the art to provide an improved dentifrice composition capable of enhancing the delivery and bioavailability of metal ions at the oral surfaces during brushing of the teeth when using the dentifrice.

There is a further need to enhance the delivery and bioavailability of metal ions such as zinc, stannous, and copper from a dentifrice, while maintaining stability in a low water dentifrice.

BRIEF SUMMARY

In a first aspect the present invention provides a dentifrice composition comprising an orally acceptable vehicle and at least one source of metal ions in a polymer matrix, the metal being selected from zinc, stannous, copper or combinations thereof the at least one source of metal ions comprising from 10 to 75 wt % of the total weight of the polymer matrix and the at least one source of metal ions, and wherein the dentifrice composition comprises less than 10 wt % water based on the total weight of the dentifrice composition.

In a second aspect the present invention provides a method of stabilizing at least one source of metal ions in a dentifrice composition comprising an orally acceptable vehicle, the method comprising the steps of: providing at least one source of metal ions in a polymer matrix, the metal being selected from zinc, stannous, copper or combinations thereof, the at least one source of metal ions comprising from 10 to 75 wt % of the total weight of the polymer matrix; and combining the polymer matrix with the orally acceptable vehicle to form a stabilized dentifrice composition comprising less than 10 wt % water based on the total weight of the dentifrice composition.

The orally acceptable vehicle may include at least one phosphate compound.

The present invention is predicated on the finding by the present inventors that therapeutically effective amounts of metal ions can be retained in a highly stabilized form in dentifrice compositions if the dentifrice composition has a low water content and the metal ions are in a polymer matrix which can act to protect the metal ions against premature reaction with or degradation by other components in the vehicle of the dentifrice composition.

DETAILED DESCRIPTION

It should be understood that the detailed description and specific examples, while indicating embodiments of the invention, are intended for purposes of illustration only and are not intended to limit the scope of the invention.

The following definitions and non-limiting guidelines must be considered in reviewing the description of this invention set forth herein. The headings (such as "Background of the Invention" and "Summary,") and sub-headings (such as "Compositions") used herein are intended only for general organization of topics within the disclosure of the invention, and are not intended to limit the disclosure of the invention or any aspect thereof. In particular, subject matter disclosed in the "Background of the Invention" may include aspects of technology within the scope of the invention, and may not constitute a recitation of prior art. Subject matter disclosed in the "Summary" is not an exhaustive or complete disclosure of the entire scope of the invention or any embodiments thereof. Classification or discussion of a material within a section of this specification as having a particular utility (e.g., as being an "active" or a "carrier" ingredient) is made for convenience, and no inference should be drawn that the material must necessarily or solely function in accordance with its classification herein when it is used in any given composition.

The citation of references herein does not constitute an admission that those references are prior art or have any relevance to the patentability of the invention disclosed herein. Any discussion of the content of references cited in the Background of the Invention is intended merely to provide a general summary of assertions made by the authors of the references, and does not constitute an admission as to the accuracy of the content of such references.

The description and specific examples, while indicating embodiments of the invention, are intended for purposes of illustration only and are not intended to limit the scope of the invention. Moreover, recitation of multiple embodiments having stated features is not intended to exclude other embodiments having additional features, or other embodiments incorporating different combinations the stated of features. Specific Examples are provided for illustrative purposes of how to make and use the compositions and methods of this invention and, unless explicitly stated otherwise, are not intended to be a representation that given embodiments of this invention have, or have not, been made or tested.

As used herein, the words "preferred" and "preferably" refer to embodiments of the invention that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention. In addition, the compositions and the methods may comprise, consist essentially of, or consist of the elements described therein.

As used herein, the word "include," and its variants, is intended to be non-limiting, such that recitation of items in a list is not to the exclusion of other like items that may also be useful in the materials, compositions, devices, and methods of this invention.

As used herein, the term "about," when applied to the value for a parameter of a composition or method of this invention, indicates that the calculation or the measurement of the value allows some slight imprecision without having a substantial effect on the chemical or physical attributes of the composition or method. If, for some reason, the imprecision provided by "about" is not otherwise understood in the art with this ordinary meaning, then "about" as used herein indicates a possible variation of up to 5% in the value.

As referred to herein, all compositional percentages are by weight of the total composition, unless otherwise specified.

Compositions

In an embodiment, the present invention provides a dentifrice composition comprising an orally acceptable vehicle and at least one source of metal ions in a polymer matrix, the metal being selected from zinc, stannous, copper or combinations thereof, the at least one source of metal ions comprising from 10 to 75 wt % of the total weight of the polymer matrix and the at least one source of metal ions, and wherein the dentifrice composition comprises less than 10 wt % water based on the total weight of the dentifrice composition.

Optionally, the at least one source of metal ions comprises from 20 to 60 wt % of the total weight of the polymer matrix and the at least one source of metal ions.

The polymer matrix and the at least one source of metal ions may comprise from 1 to 5 wt % of the total weight of the dentifrice composition, optionally from 1 to 2 wt % of the total weight of the dentifrice composition.

In some embodiments, the source of metal ions comprises at least one of zinc citrate, zinc lactate, zinc gluconate or zinc oxide. In other embodiments, the source of metal ions comprises at least one of stannous chloride, stannous fluoride or stannous oxide. In a further embodiment, the source of metal ions comprises copper sulfate. Any of these sources may be combined in any combination thereof.

The dentifrice composition may comprise at least one phosphate selected from sodium tripolyphosphate and tetrasodium polyphosphate. Typically, the dentifrice composition comprises sodium tripolyphosphate in an amount of from 1 to 5 wt % based on the total weight of the dentifrice composition and tetrasodium polyphosphate in an amount of from 0.25 to 5 wt % based on the total weight of the dentifrice composition.

In some embodiments, the source of metal ions comprises zinc citrate which comprises from 20 to 60 wt % of the total weight of the polymer matrix and the at least one source of metal ions, and the polymer matrix and the at least one source of metal ions comprise from 1 to 5 wt % of the total weight of the dentifrice composition.

The dentifrice composition may be a toothpaste or a gel.

In an embodiment, the present invention provides a method of stabilizing at least one source of metal ions in a dentifrice composition comprising an orally acceptable vehicle, the method comprising the steps of: providing at least one source of metal ions in a polymer matrix, the metal being selected from zinc, stannous, copper or combinations thereof, the at least one source of metal ions comprising from 10 to 75 wt % of the total weight of the polymer matrix; and combining the polymer matrix with the orally acceptable vehicle to form a stabilized dentifrice composition comprising less than 10 wt % water based on the total weight of the dentifrice composition.

The orally acceptable vehicle may optionally include at least one phosphate compound. The at least one phosphate compound may be selected from at least one of sodium tripolyphosphate and tetrasodium polyphosphate.

The dentifrice composition may comprises sodium tripolyphosphate in an amount of from 1 to 5 wt % based on the total weight of the dentifrice composition and tetrasodium polyphosphate in an amount of from 0.25 to 5 wt % based on the total weight of the dentifrice composition.

The at least one source of metal ions may comprise from 20 to 60 wt % of the total weight of the polymer matrix and the at least one source of metal ions.

The polymer matrix and the at least one source of metal ions may comprise from 1 to 5 wt % of the total weight of the dentifrice composition, optionally from 1 to 2 wt % of the total weight of the dentifrice composition.

The source of metal ions may comprise at least one of zinc citrate, zinc lactate, zinc gluconate, zinc oxide, stannous chloride, stannous fluoride, stannous oxide or copper sulfate, or a combination thereof.

The composition according to the preferred embodiments of the present invention can provide a low water dentifrice composition, containing a source of metal ion selected from at least one of zinc, stannous, copper or mixture thereof, where the ion source is encapsulated in a polymer matrix. The dentifrice composition has a sufficiently low water content to keep the metal ion entrapped in the polymer matrix in the dentifrice, but the polymer matrix will quickly dissolve during brushing of the teeth using the dentifrice, thereby releasing the metal ions to the oral cavity. The present inventors have surprisingly found that the polymer matrix can encapsulate relatively large, therapeutic amounts of the source of metal ions and exhibit long term stability, without excessive solution of the metal ions into the vehicle of the dentifrice composition which would reduce the delivery and bioavailability of the metal ions during use.

This invention therefore relates to a low water dentifrice composition containing a source of metal ion comprising from zinc, stannous, copper or mixture thereof, where the ion source is encapsulated in a polymer matrix (e.g. in the form of a film).

The polymer matrix described herein is preferably a water hydratable film having a matrix comprised of a water soluble hydroxyl alkyl cellulose polymer having mucoadhesive properties. The polymer matrix is used to entrap soluble and insoluble metal ion sources such as zinc (e.g. zinc citrate, zinc lactate, zinc gluconate, zinc oxide), stannous (e.g. stannous chloride, stannous fluoride, stannous oxide) or copper (copper sulfate).

The metal ion source would not remain in the polymer matrix in a conventional dentifrice (>10% $H_2O$) due to either moderate solubility in water or interactions with dentifrice ingredients such as surfactants, phosphates, or other chelating ingredients.

In this invention the dentifrice composition has a sufficiently low water content, (<10% in $H_2O$), to keep the metal ion source from becoming soluble in the formulation, but will quickly become soluble once the polymer matrix is dissolved during brushing.

Without wishing to be bound by any theory of operation, it is thought that are several advantages to the low water dentifrice composition as compared to high water content dentifrice compositions of the prior art.

First, due to the mucoadhesive properties of the polymer, the polymer matrix can potentially increase the delivery of the ion to the oral cavity, enhancing its bioavailability.

Second, the polymer matrix can protect the metal ion in the formulation from undesirable ingredient interactions which would otherwise hinder delivery. Incorporating these metal ion-containing films into a low water formula keeps the metal ion in its least soluble form until the point of delivery, allowing for controlled release of the metal ion from the formulation.

Enhanced delivery/bioavailability of these metal ions can lead to enhanced cosmetic (fresh breath, anti-tartar, anti-erosion) and/or therapeutic (anti-plaque, anti-gingivitis, anti-hypersensitivity, anti-bacterial, antimicrobial) benefits versus a standard dentifrice. The metal ions and their salts (e.g., zinc chloride, zinc lactate, zinc citrate, stannous fluoride, and stannous chloride) may in particular provide one or more of these cosmetic and/or therapeutic effects in the dentifrice compositions of the present invention.

The polymer matrix is preferably in the form of film flakes. Such film flakes for use in the compositions of the present invention are typically formed from a matrix comprised of hydroxyalkyl cellulose, such as hydroxyalkyl methylcellulose and starch. The at least one source of metal ions is entrained or encapsulated in the polymer matrix film. Other agents which may be entrained or encapsulated in the polymer matrix film include at least one of a colorant such a dye or pigment, a flavorant, sweetener and/or a therapeutic agent such as an antibacterial agent or a breath freshening agent. The film matrix can further comprise water, additional film forming agents, plasticizing agents, surfactants and emulsifying agents.

Preparation of Film Matrix

In preparing the film matrix for use in the dentifrice compositions according to the present invention the hydroxyalkyl cellulose, such as hydroxyalkylmethyl cellulose, the at least one source of metal ions, a starch ingredient, a colorant, flavor, sweetener and/or therapeutic agents and other film forming ingredients are dissolved in a compatible solvent to form a film forming composition. The film forming composition is cast on a releasable carrier and dried to form a sheet of film matrix material. The carrier material should have a surface tension which allows the film solution to spread evenly across the intended carrier width without soaking to form a destructive bond between the film and the carrier substrate. Examples of suitable carrier materials include glass, stainless steel, Teflon and polyethylene-impregnated paper. Drying of the film may be carried out at high temperature using a drying oven, drying terminal, vacuum drier, or any other suitable drying equipment which does not adversely affect the ingredients of which the film is composed.

The film thickness ranges in size from 0.5 to 10 microns and preferably 2 to 3 microns. The dried film of the present invention is then cut or punched into shaped flakes having a particle size of 0.01 to 0.50 inches preferably 0.08 to 0.25 inches.

Additional stability can be provided to the shapes formed from the dried film, by applying to the film, before shaping into flakes, a protective barrier overcoat such as a food grade shellac or ethyl cellulose.

When the film is to be used for decorative effect, the film once formed is punched into various attractive shaped flakes such as hearts, stars, diamonds and circles. The film flakes are incorporated in the base dentifrice of the present invention at a concentration of about 1 to about 5% by weight and preferably about 1 to about 2% by weight. The loading of the source of metal ions in the polymer matrix typically comprises from 20 to 60 wt % based on the combined weight of the polymer matrix and the source of metal ions.

Film Forming Agents

The major film forming agent used to prepare the film matrix of the present invention is an hydroxyalkyl cellulose such as hydroxypropyl methyl cellulose, hydroxyethylpropyl cellulose, hydroxybutyl methyl cellulose, hydroxy propyl methyl cellulose and carboxymethyl cellulose. Preferably the cellulose polymer is a low viscosity hydropropylmethyl cellulose polymer (HPMC). When HPMC is used as the film forming agent it is preferred that the HPMC have a viscosity in the range of about 1 to about 40 millipascal seconds (mPa·s) as determined as a 2% by weight aqueous solution of the HPMC at 20° C. using a Ubbelohde tube viscometer. Preferably the HPMC has a viscosity of about 3 to about 20 mPa·s at 20° C.

HPMC is available commercially from the Dow Chemical Company under the trade designation Methocel E5 LV. Methocel E5 LV is a USP grade, low viscosity HPMC having 29.1% methoxyl groups and 9% hydroxyproxyl group substitution. It is a white or off-white free-flowing dry powder. As a 2 wt. % solution in water as measured with a Ubbelohde tube viscometer it has a viscosity of 5.1 mPa·s at 20'C.

The hydroxyalkyl methyl cellulose is incorporated in the film matrix in amounts ranging from about 10 to about 60% by weight and preferably about 15 to about 40% by weight.

Cold water swellable, physically modified and pregelatenized starches are particularly useful as texture modifier to increase the stiffness of the hydroxyalkyl methyl cellulose film matrix of the present invention. In the preparation of such starch products, the granular starch is cooked in the presence of water and possibly an organic solvent at a temperature not higher than 10° C. higher than the gelatinization temperature. The obtained starch is then dried.

Pregelatinized corn starch is available commercially. A preferred starch is available under the trade designation Cerestar Polar Tex-Instant 12640 from the Cerestar Company. This Cerestar starch is a pregelaterized, stabilized and crosslinked waxy maize starch. It is readily dispersible and swellable in cold water. In its dry form, it is a white free flowing powder with an average flake size no greater than 180 micrometers and 85% of the flakes are smaller than 75 micrometers. It has a bulk density of 44 lbs/ft$^3$.

The Cerestar starch has excellent cold storage and freeze-thaw stability. It has a rapid hydration rate and can reach extremely high viscosity without cooking. It has a smooth and creamy texture similar to cook-up starches. It also has excellent paste clarity and a bland flavor.

The pregelatinized starch is present in the film matrix of the present invention in an amount ranging from about 5 to about 50% by weight and preferably about 10 to about 35% by weight.

The hydroxyalkyl cellulose to starch ratio (by weight) may vary from about 1:3 to about 4:1 and preferably about 1:1.5 to about 2.5:1.

The dentifrice composition according to the present invention may comprise an antimicrobial agent which may be selected from halogenated diphenyl ether (triclosan), herbal extracts or essential oils (e.g., rosemary extract, thymol, menthol, eucalyptol, methyl salicylate), bisguanide antiseptics (e.g., chlorhexidine, alexidine, or octenidine), phenolic antiseptics, hexetidine, povidone iodine, delmopinol, salifluor, sanguinarine, propolis, oxygenating agents (e.g., hydrogen peroxide, buffered sodium peroxyborate, or peroxycarbonate), cetyl pyridinium chloride, magnolia extract, magnolol, honokiol, butyl magnolol, propyl honokiol, and mixtures thereof. Anti-attachment agents such as Solrol also can be included, as well as plaque dispersing agents such as enzymes (papain, glucoamylase, etc.).

The composition according to the present invention may also comprise one or more further agents typically selected from an anti-plaque agent, a whitening agent, antibacterial agent, cleaning agent, a flavouring agent, a sweetening agent, adhesion agents, surfactants, foam modulators, abrasives, pH modifying agents, humectants, mouth feel agents, colorants, abrasive, tartar control (anticalculus) agent, fluoride ion source, saliva stimulating agent, nutrient and combinations thereof. Various components that may be added to the composition include, for example, a sweetening agent such as saccharin, or sodium saccharin, alcohols such as ethanol, fluoride ion sources such as sodium fluoride, as well as glycerine, sorbitol, propylene glycol, polyethylene glycols, Poloxomer polymers such as POLOXOMER 407, PLURONIC F108, (both available from BASF Corporation), alkyl polyglycoside (APG), polysorbate, PEG40, castor oil, menthol, and the like.

Flavorants among those useful herein include any material or mixture of materials operable to enhance the taste of the composition. Any orally acceptable natural or synthetic flavorant can be used, such as flavoring oils, flavoring aldehydes, esters, alcohols, similar materials, and combinations thereof. Flavorants include vanillin, sage, marjoram, parsley oil, spearmint oil, cinnamon oil, oil of wintergreen (methylsalicylate), peppermint oil, clove oil, bay oil, anise oil, eucalyptus oil, citrus oils, fruit oils and essences including those derived from lemon, orange, lime, grapefruit, apricot, banana, grape, apple, strawberry, cherry, pineapple, etc., bean- and nut-derived flavors such as coffee, cocoa, cola, peanut, almond, etc., adsorbed and encapsulated flavorants, and mixtures thereof. Also encompassed within flavorants herein are ingredients that provide fragrance and/or other sensory effect in the mouth, including cooling or warming effects. Such ingredients include menthol, menthyl acetate, menthyl lactate, camphor, eucalyptus oil, eucalyptol, anethole, eugenol, cassia, oxanone, [alpha]-irisone, propenyl guaiethol, thymol, linalool, benzaldehyde, cinnamaldehyde, N-ethyl-p-menthan-3-carboxamine, N,2,3-trimethyl-2-isopropylbutanamide, 3-1-menthoxypropane-1,2-diol, cinnamaldehyde glycerol acetal (CGA), methone glycerol acetal (MGA), and mixtures thereof. One or more flavorants are optionally present in a total amount of about 0.01% to about 5%, optionally in various embodiments from about 0.05 to about 2%, from about 0.1% to about 2.5%, and from about 0.1 to about 0.5%.

Sweetening agents among those useful herein include dextrose, polydextrose, sucrose, maltose, dextrin, dried invert sugar, mannose, xylose, ribose, fructose, levulose, galactose, corn syrup, partially hydrolyzed starch, hydrogenated starch hydrolysate, sorbitol, mannitol, xylitol, maltitol, isomalt, aspartame, neotame, saccharin and salts thereof, sucralose, dipeptide-based intense sweeteners, cyclamates, dihydrochalcones, and mixtures thereof.

Mouth-feel agents include materials imparting a desirable texture or other feeling during use of the composition.

Colorants among those useful herein include pigments, dyes, lakes and agents imparting a particular luster or reflectivity such as pearling agents. In various embodiments, colorants are operable to provide a white or light-colored coating on a dental surface, to act as an indicator of locations on a dental surface that have been effectively contacted by the composition, and/or to modify appearance, in particular color and/or opacity, of the composition to enhance attractiveness to the consumer. Any orally acceptable colorant can be used, including FD&C dyes and pigments, talc, mica, magnesium carbonate, calcium carbonate, magnesium silicate, magnesium aluminum silicate, silica, titanium dioxide, zinc oxide, red, yellow, brown and black iron oxides, ferric ammonium ferrocyanide, manganese violet, ultramarine, titaniated mica, bismuth oxychloride, and mixtures thereof. One or more colorants are optionally present in a total amount of about 0.001% to about 20%, for example about 0.01% to about 10% or about 0.1% to about 5%.

The compositions of the present invention further comprise an optional abrasive useful for example as a polishing agent. Any orally acceptable abrasive can be used, but type, fineness, (particle size) and amount of abrasive should be selected so that tooth enamel is not excessively abraded in normal use of the composition. Suitable optional abrasives include silica, for example in the form of precipitated silica or as admixed with alumina, insoluble phosphates, calcium carbonate, and mixtures thereof. Among insoluble phosphates useful as abrasives are orthophosphates, polymetaphosphates and pyrophosphates. Illustrative examples are dicalcium orthophosphate dihydrate, calcium pyrophosphate, calcium pyrophosphate, tricalcium phosphate, calcium polymetaphosphate and insoluble sodium polymetaphosphate.

The compositions of the present invention optionally comprise a tartar control (anticalculus) agent. Tartar control agents among those useful herein include salts of any of these agents, for example their alkali metal and ammonium salts: phosphates and polyphosphates (for example pyrophosphates), polyaminopropanesulfonic acid (AMPS), polyolefin sulfonates, polyolefin phosphates, diphosphonates such as azacycloalkane-2,2-diphosphonates (e.g., azacycloheptane-2,2-diphosphonic acid), N-methyl azacyclopentane-2,3-diphosphonic acid, ethane-1-hydroxy-1,1-diphosphonic acid (EHDP) and ethane-1-amino-1,1-diphosphonate, phosphonoalkane carboxylic acids and. Useful inorganic phosphate and polyphosphate salts include monobasic, dibasic and tribasic sodium phosphates, sodium tripolyphosphate, tetrapolyphosphate, mono-, di-, tri- and tetrasodium pyrophosphates, sodium trimetaphosphate, sodium hexametaphosphate and mixtures thereof.

The present invention in particular provides a dentifrice composition in which the at least one source of metal ions is stabilized in the presence of such phosphates which would otherwise tend to react with the at least one source of metal ions thereby reducing the delivery, effectiveness and bioavailability of the metal ions.

The compositions of the present invention optionally comprise a fluoride ion source and useful, for example, as an anti-caries agent. Any orally acceptable particulated fluoride ion source can be used, including potassium, sodium and ammonium fluorides and monofluorophosphates, stannous fluoride, indium fluoride, amine fluorides such as olaflur (N'-octadecyltrimethylendiamine-N,N,N'-tris(2-ethanol)-dihydrofluoride), and mixtures thereof. One or more fluoride ion sources are optionally present in an amount providing a clinically efficacious amount of soluble fluoride ion to the oral composition.

The compositions of the present invention optionally comprise a saliva stimulating agent useful, for example, in amelioration of dry mouth. Any orally acceptable saliva stimulating agent can be used, including without limitation food acids such as citric, lactic, malic, succinic, ascorbic, adipic, fumaric and tartaric acids, and mixtures thereof. One or more saliva stimulating agents are optionally present in saliva stimulating effective total amount.

The compositions of the present invention optionally comprise a nutrient. Suitable nutrients include vitamins, minerals, amino acids, and mixtures thereof. Vitamins include Vitamins C and D, thiamine, riboflavin, calcium pantothenate, niacin, folic acid, nicotinamide, pyridoxine, cyanocobalamin, para-aminobenzoic acid, bioflavonoids, and mixtures thereof. Nutritional supplements include amino acids (such as L-tryptophane, L-lysine, methionine, threonine, levocarnitine and L-carnitine), lipotropics (such as choline, inositol, betaine, and linoleic acid), and mixtures thereof.

The dentifrice composition according to the present invention comprises an orally acceptable carrier in a product such as a toothpaste or a gel. As used herein, an "orally acceptable carrier" refers to a material or combination of materials that are safe for use in the compositions of the present invention, commensurate with a reasonable benefit/risk ratio.

Preferably, specific materials and compositions to be used in this invention are, accordingly, pharmaceutically- or cosmetically-acceptable, clinically effective, and/or clinically efficacious. As used herein, such a "pharmaceutically acceptable" or "cosmetically acceptable", "clinically effective", and/or "clinically efficacious" component is one that is suitable for use with humans and/or animals and is provided in an appropriate amount (a clinically efficacious amount) to provide the desired therapeutic, prophylactic, sensory, decorative, or cosmetic benefit without undue adverse side effects (such as toxicity, irritation, and allergic response) commensurate with a reasonable benefit/risk ratio.

Methods of Use

The dentifrice composition according to the present invention may be administered to or applied to a human or other animal subject. The composition is suitable for administration or application to the oral cavity of a human or animal subject.

Each and every reference cited herein is hereby incorporated by reference in its entirety. Various embodiments now will be described with reference to the following non-limiting examples

EXAMPLES

Example 1

Zinc citrate is a zinc salt which has moderate solubility in water. A film of water soluble hydroxyl alkyl cellulose polymer was prepared using the process described hereinabove. Zinc citrate was added to the film at a 36 wt % loading, i.e. the zinc citrate comprised 36 wt % of the total weight of the combination of the film and the zinc citrate.

This film was then added to a low water (<10 wt %) dentifrice having the composition of Composition A shown in Table 1. This provided 2.0 wt % zinc citrate in the dentifrice. Table 1 illustrates examples of dentifrice compositions formulated with such films carrying a source of metal ions and in combination with other known oral care active ingredients. The dentifrice composition included 0.5 wt % tetrasodium pyrophosphate, which is known to react with zinc ions when the two are present in a dentifrice composition.

To quantify the stability of the metal ion, i.e. zinc in this Example, in the polymer matrix after addition to the dentifrice composition, the dentifrice Composition A was subjected to an accelerated aging test in which the dentifrice was stored at an elevated temperature of 40° C. for a period of up 3 months, and at the end of each month the percentage amount of the original zinc remaining in the film was measured.

In the measurement process, the polymer film was removed from the dentifrice and the dentifrice was analyzed to see if any metal ion has migrated into it. The result was used to calculate the amount of zinc remaining in the polymer matrix after the respective aging period of the dentifrice. A 1:1 by weight dentifrice to glycerin slurry was made. Glycerin was used because the polymer film does not swell or dissolve in the glycerin humectant. The slurry was passed through a filter to separate the polymer film from the dentifrice. The dentifrice slurry was analyzed by atomic absorption for zinc content. The amount of zinc remaining in the polymer matrix, proportional to the original amount, was calculated. The results are shown in Table 2.

It was found that, approximately two thirds (66 wt %) of the zinc citrate remained in the polymer matrix even after three months under accelerated aging conditions.

This demonstrated the ability of a dentifrice formulation with <10 wt % water to preserve the encapsulation of a soluble metal ion by a polymer matrix, in particular in a film thereof, even when the dentifrice composition included a phosphate such as tetrasodium pyrophosphate.

Example 2

A second film containing zinc oxide as the zinc salt incorporated into a film of water soluble hydroxyl alkyl cellulose polymer was prepared using the process described hereinabove. The zinc oxide was added to the film at a 50 wt % loading, i.e. the zinc oxide comprised 50 wt % of the total weight of the combination of the film and the zinc oxide. The film also included menthol as a flavorant.

This film was then added to a low water (<10 wt %) dentifrice having the composition of Composition B shown in Table 1. This provided 2.0 wt % zinc oxide in the dentifrice. The dentifrice composition included not only 3.0 wt % sodium tripolyphosphate but also 0.5 wt % tetrasodium pyrophosphate, both of which are known to react with zinc ions when the two are present in a dentifrice composition.

Again, the stability of the metal ion was determined using the aging test described in Example 1. The results are shown in Table 3.

It was found that approximately 85 wt % of the zinc citrate remained in the polymer matrix even after three months under accelerated aging conditions.

This demonstrated the ability of a dentifrice formulation with <10 wt % water to preserve the encapsulation of a soluble metal ion by a polymer matrix, in particular in a film thereof, even when the dentifrice composition included sodium tripolyphosphate and tetrasodium pyrophosphate.

Example 3

A third film containing zinc oxide as the zinc salt incorporated into a film of water soluble hydroxyl alkyl cellulose polymer was prepared using the process described hereinabove. The zinc oxide was added to the film at a 50 wt % loading, i.e. the zinc oxide comprised 50 wt % of the total weight of the combination of the film and the zinc oxide. The film also included menthol as a flavorant.

A fourth film containing zinc citrate trihydrate as the zinc salt incorporated into a film of water soluble hydroxyl alkyl cellulose polymer was prepared using the process described hereinabove. The zinc citrate trihydrate was added to the film at a 36 wt % loading, i.e. the zinc citrate trihydrate comprised 36 wt % of the total weight of the combination of the film and the zinc citrate trihydrate.

This film was then added to a low water (<10 wt %) dentifrice having the composition of Composition C shown in Table 1, which additionally contained zinc citrate trihydrate as a zinc salt incorporated into the dentifrice composition. This provided in the entire dentifrice both 2.0 wt % zinc citrate trihydrate, present in the dentifrice carrier, and 1.0 wt % zinc oxide, present in the film carried in the dentifrice carrier. The dentifrice composition included not only 3.0 wt % sodium tripolyphosphate but also 2.0 wt % tetrasodium pyrophosphate, both of which are known to react with zinc ions when the two are present in a dentifrice composition.

Again, the stability of the metal ion in the film was determined using the aging test described in Example 1. The results are shown in Table 3.

It was found that approximately all, i.e. about 100 wt %, of the zinc oxide remained in the polymer matrix even after three months under accelerated aging conditions, even when pyrophosphate salts and zinc citrate are present in the dentifrice composition, in particular the carrier.

This demonstrated the ability of a dentifrice formulation with <10 wt % water to preserve the encapsulation of a soluble metal ion by a polymer matrix, in particular in a film thereof, even when the dentifrice composition included sodium tripolyphosphate, tetrasodium pyrophosphate and zinc citrate.

Comparative Examples 1 and 2

A traditional dentifrice, containing from 20 to 30 wt % water, was formulated. The dentifrice contained a zinc chelator for stabilizing zinc salts and 2 wt % tetrasodium pyrophosphate.

In Comparative Example 1 a film as prepared for Example 1 and containing ZnO at a 50% loading was prepared and 2 wt % film was added to the dentifrice to provide 1 wt % ZnO in the dentifrice composition.

In Comparative Example 2 a film as prepared for Example 1 and containing ZnO at a 50% loading was prepared and 2 wt % film was added to the dentifrice to provide 1 wt % ZnO in the dentifrice composition. The dentifrice composition contained 2 wt % zinc citrate in the carrier for the film.

Both dentifrices were subjected to 7 months aging at room temperature.

At the end of the aging test, over 50% of the zinc oxide was removed from the polymer film.

The Examples and Comparative Examples demonstrate that a dentifrice with <10% water is adapted to keep zinc oxide in a polymer film even in a dentifrice containing pyrophosphate salts. This also applies, as shown by Example 3 and Comparative Example 2, even when zinc citrate is additionally present the dentifrice composition containing pyrophosphate salts.

TABLE 1

Dentifrice Compositions

| Component | A % w/w | B % w/w | C % w/w |
|---|---|---|---|
| 99.0%-101.0% Vegetable Glycerin-USP and EP | 59.537 | 56.457 | 50.457 |
| Dental Type Silica (Zeodent 114) Abrasive | 10 | 10 | 12.0 |
| Dental Type Silica-Zeodent | 10 | 10 | 12.0 |

TABLE 1-continued

Dentifrice Compositions

| Component | A % w/w | B % w/w | C % w/w |
|---|---|---|---|
| 105-High Cleaning Silica | | | |
| Zeodent 165-Synth Amorphous PPT Silica | 5.0 | 5.0 | |
| Polyethylene Glycol 600 | 3.0 | 3.0 | 7.0 |
| Sodium Tripolyphosphate (STPP) | | 3.0 | 3.0 |
| 36% loading Zinc Citrate trihydrate Film | | | 2.0 |
| 50% loading Zinc Oxide Film w/Menthol | | 2.0 | 1.0 |
| 36% loading Zinc Citrate Film | 2.0 | | |
| Sodium Lauryl Sulfate Powder-NF | 1.5 | 1.5 | 1.5 |
| Flavor | 1.15 | 1.2 | 1.2 |
| Poly(vinylpyrrolidone) Polyclar 10 | | | 1.0 |
| Sodium Fluoride USP | 0.243 | 0.243 | 0.243 |
| Tetrasodium Pyrophosphate (TSPP) | 0.5 | 0.5 | 2.0 |
| Sodium CMC-12 Type USP or Type 7-500T | 0.6 | 0.6 | |
| Sodium Saccharin USP | 0.270 | 0.5 | 0.3 |
| Xanthan Gum-NF | 0.2 | 0.2 | 0.3 |
| Demineralized Water | qs, <10% | qs, <10% | qs, <10% |

TABLE 2

Wt % Zn Citrate remaining in a polymer film after accelerated aging in dentifrice.

| Formula | 1 Month 40° C. aging wt % Zn in film | 2 Month 40° C. aging wt % Zn in film | 3 Month 40° C. aging wt % Zn in film |
|---|---|---|---|
| A | 78% | 71% | 66% |

TABLE 3

Wt % Zinc oxide remaining in a polymer film after accelerated aging in dentifrice.

| Formula | 1 Month 40° C. aging % Zn in film | 2 Month 40° C. aging % Zn in film | 3 Month 40° C. aging % Zn in film |
|---|---|---|---|
| B (3% STPP) | 95% | 95% | 85% |
| C (2% TSPP, 3% STPP, 2% Zinc Citrate) | 100% | 98% | 100% |

What is claimed is:

1. A dentifrice composition comprising
an orally acceptable vehicle and
at least one source of metal ions in a polymer matrix,
the metal being selected from zinc, stannous, copper or combinations thereof,
the at least one source of metal ions comprising from 10 to 75 wt % of the total weight of the polymer matrix, and
wherein the dentifrice composition comprises less than 10 wt % water based on the total weight of the dentifrice composition; and
wherein the polymer matrix and the at least one source of metal ions comprise from 1 to 5 wt % of the total weight of the dentifrice composition.

2. The dentifrice composition according to claim 1 wherein the at least one source of metal ions comprises from 20 to 60 wt % of the total weight of the polymer matrix and the at least one source of metal ions.

3. The dentifrice composition according to claim 1, wherein the polymer matrix and the at least one source of metal ions comprise from 1 wt. % to 2 wt. % of the total weight of the dentifrice composition.

4. The dentifrice composition according to claim 1 wherein the source of metal ions comprises at least one of zinc citrate, zinc lactate, zinc gluconate or zinc oxide.

5. The dentifrice composition according to claim 1 wherein the source of metal ions comprises at least one of stannous chloride, stannous fluoride or stannous oxide.

6. The dentifrice composition according to claim 1 wherein the source of metal ions comprises copper sulfate.

7. The dentifrice composition according to claim 1 wherein the dentifrice composition comprises at least one phosphate selected from at least one of sodium tripolyphosphate and tetrasodium polyphosphate.

8. The dentifrice composition according to claim 2 wherein the dentifrice composition comprises
    sodium tripolyphosphate in an amount of from 1 to 5 wt % based on the total weight of the dentifrice composition and
    tetrasodium polyphosphate in an amount of from 0.25 to 5 wt % based on the total weight of the dentifrice composition.

9. The dentifrice composition according to claim 7 wherein
    the source of metal ions comprises zinc citrate which comprises from 20 to 60 wt % of the total weight of the polymer matrix and the at least one source of metal ions, and
    the polymer matrix and the at least one source of metal ions comprise from 1 to 5 wt % of the total weight of the dentifrice composition.

10. The dentifrice composition according to claim 1 wherein
    the dentifrice composition comprises at least one of zinc oxide and zinc citrate in the polymer matrix,
    the polymer matrix comprises a film,
    the dentifrice composition further comprises a carrier for the film, and
    the carrier comprises at least one phosphate selected from at least one of sodium tripolyphosphate and tetrasodium polyphosphate.

11. The dentifrice composition according to claim 10 wherein the carrier further comprises zinc citrate.

12. The dentifrice composition according to claim 1, which is a toothpaste or a gel.

13. A method of stabilizing at least one source of metal ions in a dentifrice composition comprising an orally acceptable vehicle including at least one phosphate compound, the method comprising the steps of:
    providing at least one source of metal ions in a polymer matrix,
        the metal being selected from zinc, stannous, copper or combinations thereof,
        the at least one source of metal ions comprising from 10 to 75 wt % of the total weight of the polymer matrix; and
    combining the polymer matrix with the orally acceptable vehicle to form a stabilized dentifrice composition comprising less than 10 wt % water based on the total weight of the dentifrice composition.

14. The method according to claim 13 wherein the orally acceptable vehicle includes at least one phosphate compound, the at least one phosphate compound being selected from at least one of sodium tripolyphosphate and tetrasodium polyphosphate.

15. The method according to claim 14 wherein the dentifrice composition comprises
    sodium tripolyphosphate in an amount of from 1 to 5 wt % based on the total weight of the dentifrice composition and
    tetrasodium polyphosphate in an amount of from 0.25 to 5 wt % based on the total weight of the dentifrice composition.

16. The method according to claim 13 wherein the at least one source of metal ions comprises from 20 to 60 wt % of the total weight of the polymer matrix and the at least one source of metal ions.

17. The method according to claim 13, wherein the polymer matrix and the at least one source of metal ions comprise from 1 to 5 wt % of the total weight of the dentifrice composition.

18. The method according to claim 17, wherein the polymer matrix and the at least one source of metal ions comprise from 1 to 2 wt % of the total weight of the dentifrice composition.

19. The method according to claim 13 wherein the source of metal ions comprises at least one of zinc citrate, zinc lactate, zinc gluconate, zinc oxide, stannous chloride, stannous fluoride, stannous oxide or copper sulfate, or a combination thereof.

20. The dentifrice composition according to claim 8, wherein the source of metal ions comprises at least one of zinc citrate, zinc lactate, zinc gluconate or zinc oxide.

* * * * *